(12) United States Patent
De Gussem

(10) Patent No.: US 8,299,037 B2
(45) Date of Patent: Oct. 30, 2012

(54) FEED OR PHARMACEUTICAL COMPOSITION COMPRISING APRAMYCIN OR AN ADEQUATE SALT THEREOF

(75) Inventor: Jeroen De Gussem, Erpe-Mere (BE)

(73) Assignee: Poulpharm B.V.B.A., Erpe-Mere (BE)

( * ) Notice: Subject to any disclaimer, the term of this patent is extended or adjusted under 35 U.S.C. 154(b) by 177 days.

(21) Appl. No.: 12/596,644

(22) PCT Filed: Apr. 19, 2007

(86) PCT No.: PCT/EP2007/053861
§ 371 (c)(1),
(2), (4) Date: Oct. 19, 2009

(87) PCT Pub. No.: WO2008/128566
PCT Pub. Date: Oct. 30, 2008

(65) Prior Publication Data
US 2010/0144656 A1    Jun. 10, 2010

(51) Int. Cl.
*A61K 31/70* (2006.01)
(52) U.S. Cl. ............................................. 514/40; 514/41
(58) Field of Classification Search .................... None
See application file for complete search history.

(56) References Cited

U.S. PATENT DOCUMENTS

| | | |
|---|---|---|
| 3,691,279 A | 9/1972 | Thompson et al. |
| 4,379,781 A | 4/1983 | Hull et al. |
| 6,876,767 B1 | 4/2005 | Crossling |

FOREIGN PATENT DOCUMENTS

| | | |
|---|---|---|
| EP | 0 032 304 A1 | 7/1981 |
| EP | 1 210 950 A1 | 6/2002 |

OTHER PUBLICATIONS

McDougald et al., "Blackhead disease in turkeys: Direct transmission of *Histomonas meleagridis* from bird to bird in a laboratory model," *Avian Diseases* (2005) 49: 328-331.
Hu et al., "The efficacy of some drugs with known anti protozoal activity against *Histomonas meleagridis* in chickens," *Verterinary Parasitology* (2004) 121: 233-238.
McDougald, L.R., "Research on the epidemiology and pathogenicity of histomoniasis in chickens and turkeys," *WPSA, Meeting of Working Group 10 (Turkey)* (2003) Berlin, Germany.
Ryden et al., "The in vitro activity of apramycin, a new aminocyclitol antibiotic," *Journal of Antimicrobial Chemotherapy* (1977) 3: 609-613.
Afifi et al., "Kinetic disposition, systemic bioavailability and tissue distribution of apramycin in broiler chickens," *Research in Veterinary Science* (1997) 62: 249-252. XP002461344.
McDougald, L.R., "Blackhead disease (Histomoniasis) in Poultry: A Critical Review," *Avian Diseases* (2005) 49 (4): 462-476. XP009069336.
Hu et al., "Effect of anticoccidials and antibiotics on the control of blackhead disease in broiler breeder pullets," *Journal of Applied Poultry Research* (2002) 11: 351-357. XP002461344.
Friedlin et al., "Apramycin minimal inhibitory concentrations for avian *Escherichia-coli* and serum levels after intramuscular injection in turkeys," *Journal of Veterinary Pharmacology and Therapeutics* (1985) 8 (1): 105-109 XP002461346.

*Primary Examiner* — Elli Peselev
(74) *Attorney, Agent, or Firm* — Merchant & Gould P.C.

(57) ABSTRACT

An apramycin containing supplement feeding stuff for poultry and is used for the prophylaxis and/or the treatment of histomoniasis.

14 Claims, 2 Drawing Sheets

Figure 1:
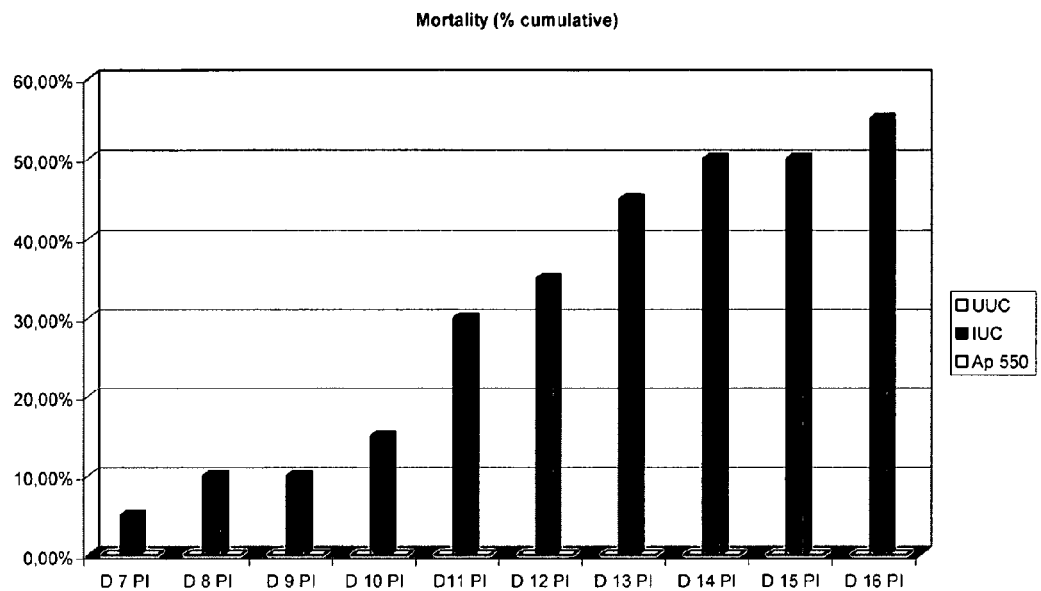

FEED OR PHARMACEUTICAL COMPOSITION COMPRISING APRAMYCIN OR AN ADEQUATE SALT THEREOF

This application is a National Stage Application of PCT/EP2007/053861, filed Apr. 19, 2007, and which application is incorporated herein by reference. To the extent appropriate, a claim of priority is made to the above disclosed application.

FIELD OF THE INVENTION

The present invention is related to apramycin containing supplement feeding stuff for poultry and its use for the prophylaxis and/or the treatment of histomoniasis.

BACKGROUND OF THE INVENTION

*Histomonas meleagridis* is a protozoan obligate parasite of poultry causing the severe disease histomoniasis, also known as enterohepatitis or blackhead. The epidemiology of the disease in a population varies from mild and slumbering to severe and acute outbreaks. Histomoniasis is characterised by depressed animals, loss of weight, yellow fluid droppings and severe necrotic lesions in caeca and liver causing pain, suffering and death. Turkeys are most sensitive to the disease with reports of 100% mortality within one flock but also broiler chickens and laying hens show mortality up to 20% accompanied by high morbidity and decreased Zootechnical parameters. Also other poultry species are susceptible for histomoniasis.

In nature infection of birds occurs normally by infestation of the intermediate host *Heterakis gallinarum*. *H. gallinarum* is a caecal parasitic nematode of poultry. *H. meleagridis* nestle in the nematode eggs to obtain protection against environmental impact. *H. meleagridis* is very fragile and can only survive for a very short period in the outer world but protected in the nematode egg the parasite can stay infectious for long time. When the infected worm or worm eggs are taken up the *H. meleagridis* remains protected against crop and stomach activity and is released in the caeca of the host by excretion or digesting of the worm or larvae. After a reproduction period in the lumen of the caeca the parasite penetrates the gut wall and travels through the bloodstream to the liver.

Domestic fowl however can be infected without the presence of *H. gallinarum*. In poultry houses temperature and climate conditions allows *H. meleagridis* to survive a few hours in the environment. Because of the high bird density the chance for the parasite to be picked by a next host is realistic. The transmission of the parasite is by direct contact of the cloaca with contaminated faeces of infected birds (1: McDougald & Fuller, 2005).

The aminoglycosides, also aminocyclitols, are a group of bactericidal antibiotics derived from the genus *Streptomyces* or *Micromonospora* (gentamicin and sisomicin). They are polycationic compounds with cyclic amino-sugars attached by glycosidic linkages. They all have a similar antimicrobial spectrum, broadly similar toxicological features and pharmacokinetics (J. F. Prescott & J. Desmond Baggot: Antimicrobial Therapy in Veterinary Medicine. Blackwell Scientific Publications, The Merck Index, Fourteenth Edition, Martindale, The ExtraPharmacopoeia. The Pharmaceutical Press and N. H. Booth & L. E. McDonald, Veterinary Pharmacology and Therapeutics. Iowa State University Press/AMES).

Apramycin ($C_{21}H_{41}N_5O_{11}$) (cas-37321-09-8) is an aminoglycoside antibiotic sold e.g. under the trade name Apralan® (ELANCO U.K.) produced by microorganisms of the *Streptomyces* sp. Genus (*Streptomyces tenebraius*) (Ryden R & Moore B. J. J. Antimicrob Chemother. Vol. 3 p 609 (1977)). It is structurally related to kanamycin and gentamicin and has a broad spectrum of bacterial activity.

Previous research has been conducted with limited success to use of apramycin as a chemotherapeutic agent for treatment of histomoniasis in chickens. Its use in-vivo was rendered ineffective when applied at 300 ppm in broilers. Only some reduction of liver lesions but no amelioration of caecal histomoniasis lesions or weight gain could be achieved (2: Hu & McDougald, 2002).

No significant treatment effect was seen for turkeys (3: McDougald, 2003).

SUMMARY OF THE INVENTION

In the executed experiment the inventor discovered that continuous oral supplementation of a sufficient amount of apramycin or an adequate salt thereof in a feed, possibly water, or a pharmaceutical composition, preferably in dosages below 1000, 900, 850 or 800 ppm, but higher than 50, 100, 150, 200, 250, 300, 350, 400, 450, 500, 550, 600, 650, 700 or 750 ppm, had a significant effect in preventing histomoniasis
reducing the mortality of infected birds;
reducing caecal and liver lesions.

Apramycin may e.g. be used in an amount between about 50 and about 750 ppm, preferably between about 100 and about 700, more preferably between about 160 and about 650 ppm or between about 175 and about 600 ppm. The preferred dosage of apramycin or an adequate salt thereof in a feed or pharmaceutical composition or water is about 550 ppm for obtaining an effective prophylaxis and/or treatment of histomoniasis in animals, preferably in turkeys. When used in prophylaxis, apramycin dosages as low as 100-200, 100-150 or 175-200 ppm may suffice.

The present invention is also related to a pharmaceutical composition comprising an adequate pharmaceutical carrier and a sufficient amount of apramycin or salt thereof present according to the dosages mentioned above. Advantageously, this sufficient amount corresponds to an equivalent of at least 1, 2, 3, 4, 5, 10, 15, 20, 25, 30, 35, 40, 45, 50, 55, 60, 65, 70, 75, 80, 85, 90, 95 or 100 mg/day per kg of animal (preferably turkeys) body weight. Dosages of at least 3, 4 or 5, possibly at least 10 or even 30-55 mg/day per kg of animal (preferably turkeys) body weight may be used.

This sufficient amount of this antibiotic or salt thereof or this pharmaceutical composition can be applied continuously to the animal in the feed or (drinking) water through the growth period from day 0 till slaughtering or during some critical intervals. This feed or pharmaceutical composition could be administrated to poultry species reared for reproduction or consumption.

Advantageously, the feed for poultry preferably for turkeys, that comprises an adequate feed stuff for poultry preferably for turkeys, and this sufficient amount of apramycin or salt thereof is presented in any solid or in any liquid form.

Another aspect of the present invention is related to the use of a sufficient amount of apramycin or salt thereof possibly present in a feed composition (possibly drinking water) for the manufacture of a medicament for the prophylaxis and/or the treatment of histomoniasis in poultry, preferably in turkeys.

To evaluate the efficacy of histomoniasis treatment the following parameters can be used: mortality, caecal and liver lesion scoring and excretion of new infective parasites. It is important to verify by monitoring the clinical signs and necropsy that mortality and lesions are caused by *Histomonas*

*meleagridis* and not by another factor. Lesions can be quantitatively scored as an indication for the degree of infection. The horizontal spreading of the disease from infected to non-infected birds (turkeys) into one pen can be an indicator of the excretion of new invasive parasites.

Apramycin has never been tested as a therapeutic agent against histomoniasis in turkeys. A significant effect in reducing the mortality of infected birds could be achieved with a sufficient amount of apramycin or an adequate salt thereof that was applied continuously in the feed. Turkeys were intracloacally inoculated, resembling the cloacal drinking process that is important in field conditions.

Hu & McDougald (2002) (4) showed some reduction of liver lesion scores in inoculated broiler chickens when apramycin is applied at 300 ppm in the drinking water. No amelioration was observed for the caecal lesions. The inventor discovered that apramycin or an adequate salt thereof applied continuously in the feed reduced significantly both liver and caecal lesion scores in turkeys, the most susceptible poultry species to histomoniasis.

Supplementation of a sufficient amount of apramycin in feeding stuff includes supplementation of the feed, the water, or the oral administration of a sufficient amount of apramycin containing solid or liquid form providing the required amount of intake per body weight per day. Apramycin is present and sold in sulphate form (sold under the name of Apralan (ELANCO U.K.)) but other pharmaceutical forms exist or could be obtained. The preferred dosages or concentrations do not depend of the formulation in which the active compound apramycin is presented. The present invention is not limited to a preferred application formulation of apramycin and includes all pharmaceutical feasible salts including not purified and technical grade intermediates containing apramycin or another antibiotic.

Another aspect of the present invention is related to a production method of the supplemented feed composition (feeding stuff) for poultry (preferably for turkeys) according to the invention which comprises the step of mixing a sufficient amount of apramycin or an adequate salt thereof with feed (for poultry preferably for turkeys) or water and optionally granulating the resulting mixture to obtain a powder, pellets, granules, gels or other solid or liquid forms of feed or water compositions.

Advantageously, in this method, the composition comprises technical grade of apramycin or its adequate salt obtained from a fermentation broth of apramycin producing microorganism. This technical grade of apramycin is preferably present in a solid formulation or liquid formulation that may further comprise one or more compatible carrier(s) adjuvant(s) or diluent(s).

The person skilled in the art can also select other aminoglycosides or acceptable salt thereof to be used for the same applications (same methods, with the same conditions (formulation, concentration, . . . ) as above mentioned for apramycin. Other examples of suitable aminoglycosides obtained from various microorganisms are structurally related antibiotics.

These aminoglycosides can more or less be divided in 4 main classes:
1. Streptomycin group that includes
    Streptomycin
    Streptomycin B
    Hydroxystreptomycin
    Deoxydihydrostreptomycin
    Dihydrostreptomycin
    Streptonicozid
2. Neomycin group that includes
    Neomycin
    Neomycin Undecylenate
    Neamine
    Streptonigrin
3. Kanamycin group that includes the kanamycins:
    Kanamycin
    Amikacin
    Arbekacin
    Dibekacin
    the nebramycins:
    Apramycin
    Tobramycin
    the gentamicins:
    Gentamicin
    Netilmicin
    Sisomicin
4. Spectinomycin group that includes
    Spectinomycin
    Trospectomycin The present invention is also related to a prophylaxis and/or treatment method of histomoniasis in poultry species which comprise the step of administrating to poultry the feed composition or (drinking) water according to the invention comprising an adequate pharmaceutical carrier and a sufficient amount of apramycin or an adequate salt thereof or the feed composition or water according to the invention that comprises feeding stuff for poultry and a sufficient amount of apramycin or an adequate salt thereof preferably at the above mentioned. Preferably, said method is applied to poultry species which are turkeys. In the method according to the invention the feed composition or water is supplied continuously to the animals starting from day 0 till slaughtering or during some critical intervals to poultry species reared for reproduction or consumption.

The present invention will be described in more details in the following example in reference to the enclosed figures and tables presented as a non limiting illustration of a preferred embodiment of the present invention.

SHORT DESCRIPTION OF THE FIGURES

Figure 2:
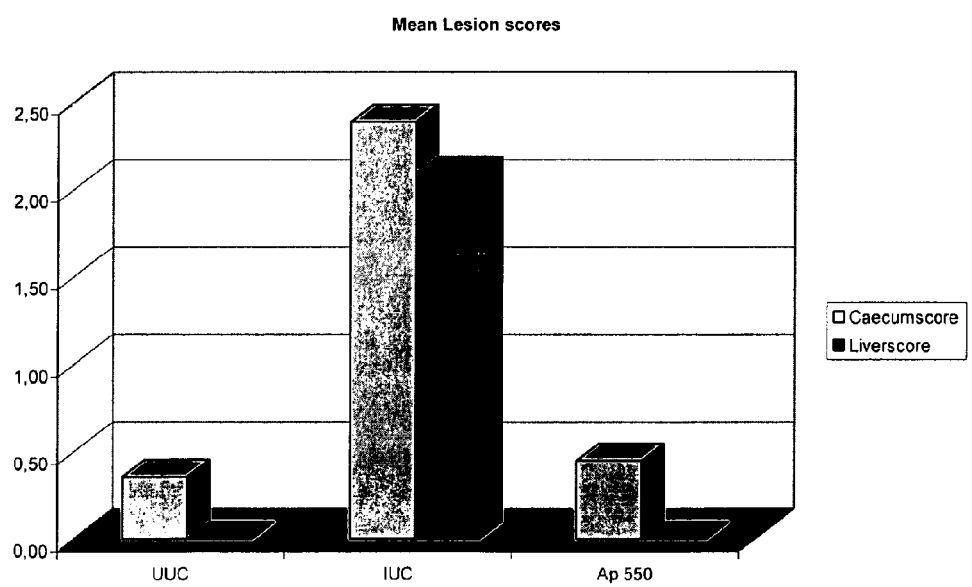
Figure 3:
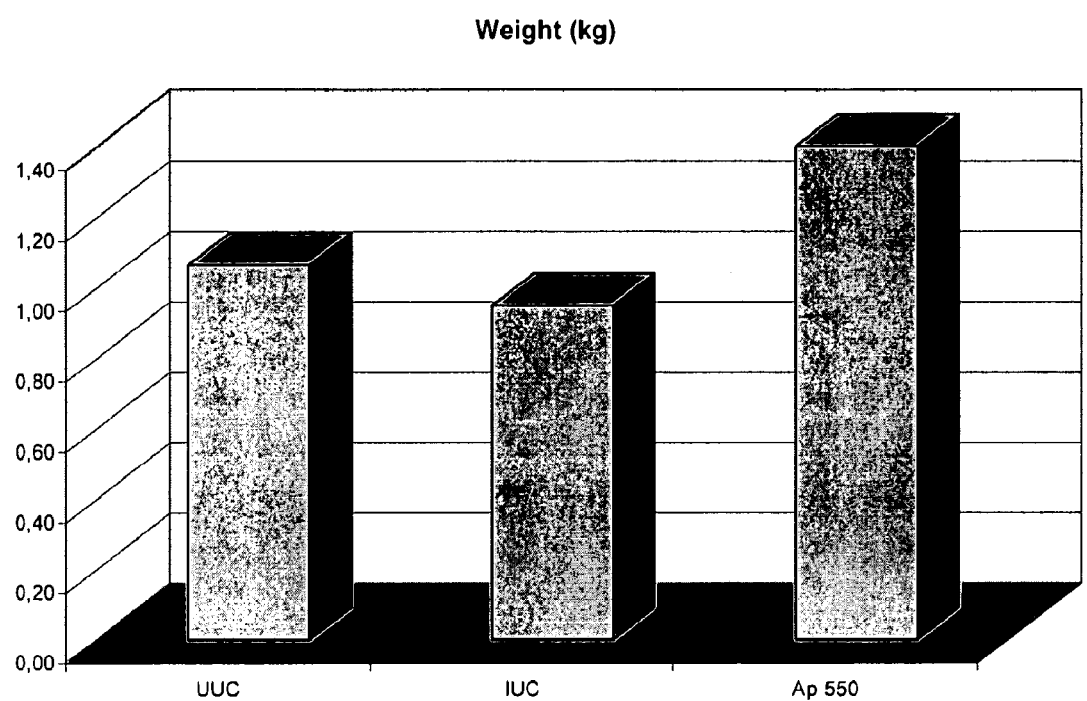

The FIG. 1 represents Mortality due to histomoniasis in DPI (Days Post Inoculation)
The FIG. 2 represents Mean lesion scores at necropsy
The FIG. 3 represents Average Weight at D38

EXAMPLES

Example 1

The objective of the study was to investigate the activity of apramycin as prophylactic agent against a *Histomonas meleagridis* strain isolated from an outbreak of histomoniasis in turkeys in Belgium (September 2005). The antibiotic (apramycin) was supplemented through the feed at 550 g of the test product/MT of feed (Ap 550) in the challenged birds. This medicated group was compared with an Infected Untreated Control (IUC) and an Uninfected Untreated Control group (UUC).

Seventy five (75) one day old male animals (turkey poults) were enrolled in the study and randomly allocated to 3 groups of 25 animals per pen. During the whole study (from day 1 to day 38), Treatment 1 (UUC) and 2 (IUC) received standard animal (turkey) feed without supplementation, whereas Treatment 3, received feed supplemented with apramycin sulphate. On day 22, Treatments 2 and 3 were inoculated intracloacally with *Histomonas meleagridis*. From that day one, the animals were clinically observed on a daily base. At the end of the study, D38, all remaining animals were euthanized and necropsied and lesion scored for caeca and liver.

All animals (turkeys) died during the challenge period were necropsied to determine the cause of death. In the UUC and apramycin group not a single animal died, whereas in the IUC 14 (56%) died, all due to histomoniasis. (see Table 1 and FIG. 1).

The lesion scores are presented in table 2 and FIG. 2.

It may be clear that apramycin does provide active protection against the infection by *Histomonas meleagridis*. Not only mortality can be prevented, also the reduction in caecal and liver lesions is proven.

Besides the clinical parameters also the Zootechnical performances are ameliorated. In table 3 the live weights at the end of the study are given and compared in FIG. 3.

Example 2

The objective of the study is to investigate the activity of different doses of apramycin for the prophylaxis and/or treatment of histomoniasis. The antibiotic (apramycin) is supplemented through the feed at the doses 50 g, 150 g, 250 g, 350 g, 450 g and 550 g of the test product/MT of feed in the challenged birds. These medicated groups are compared with an Infected Untreated Control (IUC) and an Uninfected Untreated Control group (UUC).

Eight hundred (800) one day old male animals (turkey poults) are randomly allocated to one of the eight treatment groups. All treatments are replicated for 5 times, 40 pens in total each holding 20 animals. During the whole study, Treatment 1 (UUC) and 2 (IUC) receive standard animal (turkey) feed without supplementation, whereas Treatment 3 (50 ppm), 4 (150 ppm), 5 (250 ppm), 6 (350 ppm), 7 (450 ppm) and 8 (550 ppm) receive feed supplemented with apramycin sulphate. On day 22, Treatments 2 to 8 are intracloacally inoculated with *Histomonas meleagridis*. During the challenge mortality is recorded. At the end of the study all remaining animals are euthanized and necropsied and lesion scored for caeca and liver. Also the Zootechnical parameters are recorded during the entire study.

Example 3

The objective of the study is to investigate and compare the activity of different aminoglycosides for the prophylaxis and/or treatment of histomoniasis. The antibiotics (e.g. apramycin, streptomycin, neomycin, kanamycin, gentamicin, spectinomycin) are supplemented through the feed at 250 g of the test product/MT of feed in the challenged birds. These medicated groups are compared with an Infected Untreated Control (IUC) and an Uninfected Untreated Control group (UUC).

Eight hundred (800) one day old male animals (turkey poults) are randomly allocated one of the eight treatment groups. All treatments are replicated for 5 times, 40 pens in total each holding 20 animals. During the whole study, Treatment 1 (UUC) and 2 (IUC) receive standard animal (turkey) feed without supplementation, whereas Treatment 3 (apramycin), 4 (streptomycin), 5 (neomycin), 6 (kanamycin), (gentamicin) and 8 (spectinomycin) receive feed supplemented with 250 ppm of the respective aminoglycoside. On day 22, Treatments 2 to 8 are intracloacally inoculated with *Histomonas meleagridis*. During the challenge mortality is recorded. At the end of the study all remaining animals are euthanized and necropsied and lesion scored for caeca and liver. Also the Zootechnical parameters are recorded during the entire study.

TABLE 1

Mortality due to histomoniasis in days post inoculation (DPI)
Mortality (% Cumulative)

|  | D 7 PI | D 8 PI | D 9 PI | D 10 PI | D 11 PI | D 12 PI | D 13 PI | D 14 PI | D 15 PI | D 16 PI |
|---|---|---|---|---|---|---|---|---|---|---|
| UUC | 0.00% | 0.00% | 0.00% | 0.00% | 0.00% | 0.00% | 0.00% | 0.00% | 0.00% | 0.00% |
| IUC | 5.00% | 10.00% | 10.00% | 15.00% | 30.00% | 35.00% | 45.00% | 50.00% | 50.00% | 55.00% |
| Ap 550 | 0.00% | 0.00% | 0.00% | 0.00% | 0.00% | 0.00% | 0.00% | 0.00% | 0.00% | 0.00% |

TABLE 2

Mean lesion scores at necropsy

|  | Caecum score | Liver score |
|---|---|---|
| UUC | 0.36 | 0.00 |
| IUC | 2.39 | 2.09 |
| Ap 550 | 0.45 | 0.00 |

TABLE 3

Average Weight at D40

|  | Weight (kg) |
|---|---|
| UUC | 1.07 |
| IUC | 0.95 |
| Ap 550 | 1.40 |

REFERENCES (1) L. R. McDougald & L. Fuller, 2005: Blackhead Disease in Turkeys: Direct Transmission of *Histomonas meleagridis* from Bird to Bird in a Laboratory Model. Avian Diseases 49: 328-331.

(2) J. H. Hu & L. R. McDougald, 2004: The efficacy of some drugs with known antiprotozoal activity against *Histomonas meleagridis* in chickens. Vet. Parasitol. 121(3-4):233-8

(3) L. R. McDougald, 2003: Research on the epidemiology and pathogenecity of histomoniasis in chickens and turkeys. WPSA, Meeting of working group 10, Berlin 2003.

(4) J. H. Hu & L. R. McDougald, 2002: Potential value of antibiotics and anticoccidials for control of blackhead (*Histomonas meleagridis*) in chicken. Abstract of papers from concurrent meeting of the Southern Poultry Science Society.

The invention claimed is:

1. A method for treating histomoniasis in turkeys comprising administering continuously to a turkey subject a pharmaceutical composition consisting of an adequate pharmaceutical carrier and apramycin or an adequate salt thereof as a therapeutic agent, or of a feed composition or water supply for poultry consisting of feeding stuff or water for poultry and apramycin or an adequate salt thereof as therapeutic agent.

2. The method according to claim 1 wherein the composition or water supply includes between 50 and 750 ppm of apramycin.

3. The method according to claim 2 wherein the composition or water supply includes between 175 and 600 ppm of apramycin.

4. The method according to claim 1 wherein the composition or water supply includes apramycin or an adequate salt thereof in an amount equivalent to at least 1 mg/day per kilogram of animal body weight.

5. The method according to claim 1 wherein the composition or water supply includes apramycin or an adequate salt thereof in an amount equivalent to at least 3 mg/day per kilogram of animal body weight.

6. The method according to claim 1 wherein the composition or water supply includes apramycin or an adequate salt thereof in an amount equivalent to between 30 and 55 mg/day per kilogram of animal body weight.

7. The method according to claim 1 wherein the composition comprises solid or liquid form.

8. The method according to claim 1 wherein the feed composition or water supply is supplied continuously through the growth period.

9. The method according to claim 1 wherein the feed composition or water supply is supplied starting from day 0 till slaughtering.

10. The method according to claim 1 wherein the feed composition or water supply is supplied during some critical intervals to turkeys reared for reproduction or consumption.

11. A method of treating histomoniasis in turkeys comprising continuously administering to a turkey subject a composition consisting of an adequate pharmaceutical carrier and apramycin or an adequate salt thereof as therapeutic agent or of a feed composition or water supply for poultry consisting of feeding stuff or water for poultry apramycin or an adequate salt thereof as therapeutic agent, wherein apramycin or the adequate salt thereof is in amount between 150-850 ppm.

12. A method according to claim 1, comprising administering between about 150-850 ppm apramycin per day.

13. A method for reducing mortality from histomoniasis or treating histomoniasis in turkeys comprising administering continuously to a turkey subject a pharmaceutical composition consisting of an adequate pharmaceutical carrier and apramycin or an adequate salt thereof as a therapeutic agent, or of a feed composition or water supply for poultry consisting of feeding stuff or water for poultry and apramycin or an adequate salt thereof as therapeutic agent.

14. A method for reducing caecal and liver lesions from histomoniasis or treating histomoniasis in turkeys comprising administering continuously to a turkey subject a pharmaceutical composition consisting of an adequate pharmaceutical carrier and apramycin or an adequate salt thereof as a therapeutic agent, or of a feed composition or water supply for poultry consisting of feeding stuff or water for poultry and apramycin or an adequate salt thereof as therapeutic agent.

* * * * *